United States Patent [19]

Berger et al.

[11] 4,299,917
[45] Nov. 10, 1981

[54] DIAGNOSTIC AGENTS FOR THE DETECTION OF LEUKOCYTES IN BODY FLUIDS

[75] Inventors: Dieter Berger, Viernheim; Günter Frey, Ludwigshafen; Manfred Kuhr; Wolfgang Werner, both of Mannheim, all of Fed. Rep. of Germany

[73] Assignee: Boehringer Manneheim GmbH, Mannheim, Fed. Rep. of Germany

[21] Appl. No.: 114,143

[22] Filed: Jan. 21, 1980

[30] Foreign Application Priority Data

Feb. 14, 1979 [DE] Fed. Rep. of Germany ....... 2905531

[51] Int. Cl.³ ...................... G01N 33/16; G01N 31/14
[52] U.S. Cl. .................................... 435/19; 23/230 B; 252/408; 435/23
[58] Field of Search ...................... 435/19, 23, 20, 21; 252/408; 23/230 B

[56] References Cited

U.S. PATENT DOCUMENTS

| 3,087,794 | 4/1963 | Free et al. ........................... 23/230 B |
| 3,290,117 | 12/1966 | Adams, Jr. et al. ................ 252/408 |
| 3,378,463 | 4/1968 | Guilbault et al. ..................... 435/19 |
| 3,689,364 | 9/1972 | Hartel et al. ........................... 425/19 |
| 3,715,325 | 2/1973 | Linoli et al. ........................... 435/19 |
| 3,853,472 | 12/1974 | Rittersdorf et al. .............. 23/230 B |
| 3,917,452 | 11/1975 | Rittersdorf et al. ................ 252/408 |
| 3,975,161 | 8/1976 | Svoboda et al. .................. 23/230 B |
| 4,045,290 | 8/1977 | Bulbenko et al. ..................... 425/21 |
| 4,063,894 | 12/1977 | Ogawa et al. ..................... 23/230 B |
| 4,116,774 | 9/1978 | Mimato et al. ........................ 435/23 |
| 4,188,320 | 2/1980 | Kamachi et al. ...................... 435/19 |
| 4,206,280 | 6/1980 | Gallati et al. ......................... 435/21 |
| 4,212,939 | 7/1980 | Myrick et al. ........................ 435/19 |
| 4,251,222 | 2/1981 | White ................................. 252/408 |
| 4,251,223 | 2/1981 | White ................................. 252/408 |

FOREIGN PATENT DOCUMENTS

| 2847859 | 5/1979 | Fed. Rep. of Germany ...... 252/408 |
| 2826965 | 1/1980 | Fed. Rep. of Germany ...... 252/408 |
| 50-147987 | 11/1975 | Japan ..................................... 435/21 |
| 52-17897 | 2/1977 | Japan ................................... 252/408 |

Primary Examiner—Teddy S. Gron
Attorney, Agent, or Firm—Sprung, Felfe, Horn, Lynch & Kramer

[57] ABSTRACT

This invention relates to diagnositc agents and methods for the detection of leukocytes in body fluids. In additional aspect, the invention provides a process for the production of such diagnostic agents.

24 Claims, No Drawings

DIAGNOSTIC AGENTS FOR THE DETECTION OF LEUKOCYTES IN BODY FLUIDS

The detection of leukocytes in body fluids, especially in urine, occupies an important place in the diagnosis of diseases of the kidneys and of the urogenital tract.

Hitherto, this detection has been carried out by the microscopic counting of the leukocytes in non-centrifuged urine or in urinary sediment.

It is, of course, common to both methods that only intact leukocytes can be counted. On the other hand, it is known that the rate of leukocytes lysis is subject to enormous variations, depending upon the urinary medium: thus, for example, in strongly alkaline urines, the leukocytes half life can be as low 60 minutes. This results in too low leukocyte counts or, in the case of urine samples which have been standing for quite a long time, even in falsely negative findings.

Apart from lysis errors, the quantitative microscopic determination of leukocytes in non-centrifuged, homogenized urine in a counting chamber gives quite dependable values. However, in practice, this method is seldom used since it is laborious, tiring and time-consuming and requires the use of skilled personnel.

In medical practice, the overwhelming majority of leukocyte determinations in urine are carried out according to the so-called viewing field method in the urine sediment. For this purpose, the material to be investigated (sediment) must first be obtained by centrifuging. However, other components of the urine are thereby also enriched, for example, salts and epithelial cells, which can make the microscopic counting of the leukocytes considerably more difficult. Varying sediment content and inhomogeneities of the sediment, as well as, in some cases, differing microscopic enlargement or differing optical equipment of the microscope have the result that the here usual statement of the number of leukocytes per microscopic viewing field can involve errors of several hundred percent.

Therefore, recently attempts have been made to provide a diagnostic agent with which leukocytes can be detected in body fluids in a simple and complete manner, as quickly and completely as possible. For such a leukocyte test, enzymatic reactions could possibly be used since leukocytes possess a broad spectrum of enzymatic activity.

Thus, for example, in Federal Republic of Germany Patent Applications Nos. P 28 26 965.0, P 28 36 644.1 and P 28 54 987.3, diagnostic agents are described which comprise an absorbent carrier which is impregnated with an appropriate buffer substance, conventional adjuvants and a chromogen. As chromogens, there are used, according to Federal Republic of Germany Patent Application No. P 28 26 965.0, sulphonphthalein esters of the general formula:

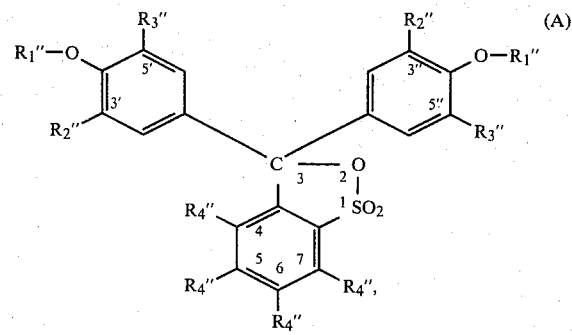

wherein $R_1''$ is a carboxylic acid residue optionally substituted by halogen or a lower alkoxy radical or is an amino acid or peptide residue provided with a nitrogen protective group conventional in peptide chemistry, $R_2''$ is a halogen atom or a lower alkyl radical and $R_3''$ and $R_4''$, which can be the same or different, are hydrogen or halogen atoms; according to Federal Republic of Germany Patent Application No. P 28 36 644.1, azo dyestuff esters of the general formula:

$$A'-N=N-B'(OR)_n \quad (B),$$

wherein $A'$ is a five- or six-membered, optionally benzoannellated residue with one or two hetero atoms selected from nitrogen, sulphur and oxygen, which can be substituted one or more times by halogen, lower alkyl and/or lower alkoxy radicals or is a phenyl radical substituted one, two or three times by lower alkyl, lower alkoxy, nitro, sulphonate and/or acylamino radicals, $B'$ is a benzene, naphthalene or quinoline radical optionally substituted once or twice by sulphonato, lower alkoxy and/or lower alkoxy-polyalkyleneoxy radicals, R is a carboxylic acid residue or an amino acid or peptide residue provided with a nitrogen protective group conventional in peptide chemistry and n is 1 or 2; and according to Federal Republic of Germany Patent Application No. P 28 54 987.3, indoxyl esters of the general formula:

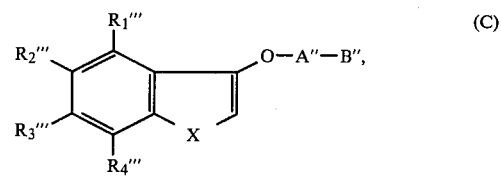

wherein $R_1'''$, $R_2'''$, $R_3'''$ and $R_4'''$, which can be the same or different, are hydrogen or halogen atoms, lower alkyl, lower alkoxy, aryl, aralkyl, aralkoxy, hydroxyl, carboxyl, carboxy lower alkoxy, aralkoxycarbonyl, aralkoxycarbonyl lower alkoxy, nitro or lower acylamino radicals or wherein two adjacent substituents represent a benzo-annellated residue optionally substituted by halogen, X is a sulphur atom or an imino group optionally substituted by a lower alkyl, aryl, aralkyl or acyl radical, A" is an amino acid or peptide residue and B" is a nitrogen protective group conventional in peptide chemistry or derived therefrom.

With the help of these diagnostic agents, the detection of esterolytic or proteolytic enzymes and especially of the esterases or proteases present in leukocytes can be carried out simply and quickly in body fluids especially in urine, via a color change.

It is an object of the present invention to find, if possible, a way of accelerating the detection reaction forming the basis of this enzymatic test.

Surprisingly, we have now found that the reaction times of these enzymatically carried out leukocyte tests can be considerably shortened when, in addition to the previously conventional adjuvants and chromogens, at least one activator is added.

Therefore, according to the present invention, there is provided a diagnostic agent for the detection of esterolytic and/or proteolytic enzymes comprising conventional adjuvants and a known esterase and/or protease substrate, characterized in that it additionally contains at least one activator.

The present invention is also concerned with the production of these diagnostic agents, as well as with the use thereof for the detection of leukocytes in body fluids and especially in urine.

The diagnostic agent according to the present invention preferably comprises an absorbent carrier, a film layer, a powder mixture, a lyophilizate, a solution or a reagent tablet which contains a known esterase and/or protease substrate, conventional additives and at least one activator.

Examples of activators which can be used according to the present invention include the following:

(a) pyridine derivatives of the general formula:

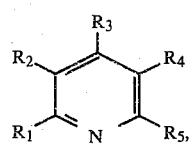
(I)

wherein $R_1$, $R_2$, $R_3$, $R_4$ and $R_5$, which can be the same or different, are hydrogen or halogen atoms, lower alkyl or lower alkoxy radicals, vinyl radicals which are substituted by an aryl radical optionally substituted one or more times by lower alkoxy, amino, alkylamino or dialkylamino, or by a heterocyclic radical and wherein two adjacent substituents can represent an indeno- or benzo-annellated residue, optionally substituted one or more times by halogen, hydroxyl, lower alkyl or lower alkoxy, which annellated residue can, in turn, carry a benzo- or pyrido-annellated residue optionally substituted by a lower alkyl radical and wherein $R_3$ can additionally represent a vinyl-quinuclidyl-carbinol radical;

(b) imidazole derivatives of the general formula:

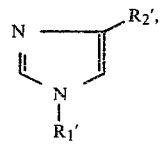
(II)

wherein $R_1'$ is a hydrogen atom, a lower alkyl radical or an aryl radical optionally substituted by a hydroxyl or an acyl radical and $R_2'$ is a hydrogen atom, an aminoalkyl, N-acylaminoalkyl or a lower aliphatic, optionally unsaturated carboxylic acid residue or a lower aliphatic α-amino acid residue, optionally acylated on the nitrogen atom;

(c) alcohols of the general formula:

$$X-A-OH \quad (III),$$

wherein X is a hydrogen atom or a hydroxyl group and A is a hydrocarbon radical;

(d) metal complexes of the general formula:

$$D_m[B(CN)_n(NO)_p] \quad (IV),$$

wherein D is an alkali metal ion, B is a heavy metal ion, m is 2, 3, 4 or 5, n is 4, 5, 6, 7 or 8 and p is 0 or 1, the number m being given by the valency of the heavy metal ion and the number n.

Halogen in the definition of the substituents $R_1$, $R_2$, $R_3$, $R_4$ and $R_5$ is to be understood to be fluorine, chlorine, bromine or iodine and preferably chlorine or bromine.

The lower alkyl and alkoxy radicals in the definition of the substituents $R_1$, $R_2$, $R_3$, $R_4$ and $R_5$, as well as the lower alkyl radicals in the definition of the substituents $R_1'$ and $R_2'$ can be straight-chained or branched and contain up to 5 and preferably up to 3 carbon atoms, the methyl, ethyl, n-propyl, isopropyl, methoxy and ethoxy radicals being especially preferred.

The hydrocarbon radical A can be straight-chained or branched, saturated or unsaturated, cyclic or acyclic and contains up to 30 and preferably 5 to 22 carbon atoms in the case of acyclic compounds and 3 to 20 and preferably 6 to 17 carbon atoms in the case of cyclic compounds.

The acyl radicals in the definition of the substituents $R_1'$ and $R_2'$ are to be understood to be aliphatic carboxylic acid residues containing up to 5 and preferably up to 3 carbon atoms, the acetyl radical being especially preferred.

The aryl radicals in the definition of the substituents $R_1$, $R_2$, $R_3$, $R_4$, $R_5$ and $R_1'$ are preferably to be understood to be phenyl or naphthyl radicals, the phenyl radical being especially preferred as the substituent $R_1'$.

The heterocyclic radical in the definition of the substituents $R_1$, $R_2$, $R_3$, $R_4$ and $R_5$ is to be understood to be a five- or six-membered radical containing up to 3 hereto atoms, the hetero atoms being nitrogen, sulphur and oxygen, the pyridyl, furyl and thienyl radicals being especially preferred.

The "lower aliphatic, optionally unsaturated carboxylic acid radical" and the "lower aliphatic α-amino acid residue optionally acylated on the nitrogen" $R_2'$ is to be understood to be a carboxylic acid residue containing up to 5 and preferably up to 3 carbon atoms or an α-amino derivative thereof, acetic acid, propionic acid, acrylic acid, L-alanine and N-acetyl-L-alanine being especially preferred.

In the activators of general formula (IV), the alkali metal ions D are preferably sodium or potassium ions and the heavy metal ion B is preferably an iron, nickel, chromium, manganese, cobalt, molybdenum or vanadium ion.

Activators which can be used according to the present invention include, for example, the following:
1. pyridine
2. 2-methylpyridine
3. 3-ethylpyridine
4. 2-bromopyridine
5. 3,5-dichloropyridine
6. 4-methoxypyridine
7. 2,6-dimethyl-4-ethoxypyridine
8. quinoline.
9. 2-methylquinoline 10. 8-methylquinoline
11. 7-isopropylquinoline
12. 2-chloroquinoline
13. 4-bromoquinoline
14. 3-methoxyquinoline
15. 6-ethoxyquinoline
16. 2-methyl-6-bromoquinoline
17. 2-methyl-4-methoxyquinoline
18. 5,7-dibromo-8-methoxyquinoline
19. isoquinoline
20. 1-methylisoquinoline
21. 3-propylisoquinoline
22. 7-methylisoquinoline
23. 1-chloroisoquinoline
24. 4-bromoisoquinoline
25. 7-methoxyisoquinoline
26. 1-methoxy-3-chloroisoquinoline
27. 1-chloro-4-methyl-5-methoxyisoquinoline
28. benzo-[b]-quinoline(=acridine)
29. benzo-[c]-quinoline(=phenanthridine)
30. 2-methylphenanthridine
31. 2-ethylphenanthridine
32. 2-propylphenanthridine
33. 2-methoxyphenanthridine
34. benzo-[f]-quinoline
35. 2-isopropyl-benzo-[f]-quinoline
36. 3-methyl-benzo-[f]-quinoline
37. 2,4-dimethylbenzo-[f]-quinoline
38. benzo-[g]-quinoline
39. 4-methylbenzo-[g]-quinoline
40. 2,4-dimethylbenzo-[g]-quinoline
41. benzo-[h]-quinoline
42. 1,7-phenanthroline
43. 2-methyl-1,7-phenanthroline
44. 2,8-dimethyl-1,7-phenanthroline
45. 4,7-phenanthroline
46. 3-methyl-4,7-phenanthroline
47. 3,8-dimethyl-4,7-phenanthroline
48. 1,10-phenanthroline
49. 2,9-dimethyl-1,10-phenanthroline
50. 4-azafluorene
51. quinine
52. quinidine
53. cinchonine
54. cinchonidine
55. cuprein
56. 2-[phenyl]-vinyl-pyridine-(2')
57. 2-[4''-methoxyphenyl]-vinyl-pyridine-(2')
58. 2-[4''-(N,N-dimethylamino)-phenyl]-vinyl-pyridine-(2')
59. bis-[2-(phenyl)-vinyl]-pyridine-(2',4')
60. 2-[naphthyl-(1'')]-vinyl-pyridine-(2')
61. 2-[pyridyl-(2'')]-vinyl-pyridine-(2')
62. 2-[pyridyl-(3'')]-vinyl-pyridine-(2')
63. 2-[pyridyl-(4'')]-vinyl-pyridine-(2')
64. 2-[furyl-(2'')]-vinyl-pyridine-(2')
65. 2-[pyridyl-(3'')]-vinyl-pyridine-(3')
66. 2-[pyridyl-(3'')]-vinyl-pyridine-(4')
67. 2-[pyridyl-(4'')]-vinyl-pyridine-(4')
68. 2-[thienyl-(2'')]-vinyl-pyridine-(4')
69. imidazole
70. 1-ethylimidazole
71. 1-phenylimidazole
72. 1-(4'-hydroxyphenyl)-imidazole
73. 1-(4'-acetylphenyl)-imidazole
74. histamine
75. N-α-acetylhistamine
76. (imidazolyl-4)-acetic acid
77. β-(imidazolyl-4)-propionic acid
78. β-(imidazolyl-4)-acrylic acid
79. L-histidine
80. N-β-acetyl-L-histidine
81. hexan-1-ol
82. heptan-1-ol
83. octan-1ol
84. nonan-1-ol
85. decan-1-ol
86. dodecan-1-ol
87. tetradecan-1-ol
88. pentadecan-1-ol
89. hexadecan-1-ol
90. heptadecan-1-ol
91. octadecan-1-ol
92. nonadecan-1-ol
93. eicosan-1-ol
94. docosan-1-ol
95. cyclohexanol
96. cyclohex-1-en-1-ol
97. cycloheptanol
98. cyclooctanol
99. cyclononanol
100. cyclodecanol
101. cyclododecanol
102. cycloheptadecanol
103. cycloheptadec-9-en-1ol
104. citronellol
105. geraniol
106. nerol
107. linalool
108. farnesol
109. nerolidol
110. cis-octadec-9-en-1-ol
111. phytol
112. phentane-1,5-diol
113. hexane-1,6-diol
114. heptane-1,7-diol
115. octane-1,8-diol
116. nonane-1,9-diol
117. decane-1,10-diol
118. dodecane-1,12-diol
119. tripotassiumhexacyanoferrate III
120. tetrapotassiumhexacyanoferrate II
121. dipotassiumtetracyanonickelate II
122. trisodiumoctacyanomolybdate V
123. disodiumpentacyanonitrosylferrate II
124. tripotassiumpentacyanonitrosylmanganate I
125. tripotassiumpentacyanonitrosylchromate I
126. tripotassiumpentacyanonitrosylcobaltate I
127. pentapotassiumpentacyanonitrosylvanadate I.

All the activators are either known compounds or can be prepared analogously to known compounds.

The compounds of general formulae (I), (II) and (IV) employed as activators according to the present invention can be used in concentrations of $10^{-4}$ to 1 mol/liter and preferably of $10^{-3}$ to $10^{-1}$ mol/liter of impregnation solution and the activators of general formula (III) can be used in the impregnation solution in a concentration of 0.5 to 10% (w/v) and preferably of 1 to 5% (w/v).

The diagnostic agents according to the present invention contain, in addition to the activators, the otherwise conventionally employed components, for example, known esterase or protease substrates, buffers and wetting agents and optionally complex-forming agents and oxidation agents. These are employed in the manner and in the concentrations described in Federal Republic of Germany Patent Applications Nos. P 28 26 965.0; P 28 36 644.1 and P 28 54 987.3.

Thus, the chromogens used as esterase or protease substrates are usually employed in concentrations of $10^{-4}$ to 1 mol/liter and preferably of $10^{-3}$ to $10^{-1}$ mol/liter of impregnation solution, coating mass or fluid to be investigated.

A further component of the diagnostic agent for the detection of esterolytic and/or proteolytic enzymes, especially of leukocyte proteases, is an appropriate buffer system. For this purpose, there can be used, for example, phosphate, borate, barbiturate, tris-(hydroxymethyl)-aminomethane(tris), 2-amino-2-methylpropane-1,3-diol(amediol) or amino acid buffers, the pH value and the capacity being so choosen that a pH value of 6 to 10 and preferably of 7 to 9 is obtained in the measurement solution or on the test strip.

A further component of a diagnostic agent for the detection of esterolytic and/or proteolytic enzymes and especially of leukocyte esterases or proteases can be a wetting agent. Non-ionic wetting agents are preferably used but amphoteric, cationic and anionic active wetting agents can also be employed, the concentration of the wetting agent being from 0.05 to 2% and preferably from 0.1 to 1%.

A further component of the diagnostic agent according to the present invention can be an appropriate complex former. It is preferable to use metal salts, for example salts of the elements iron, copper, chromium, cobalt, nickel, manganese and zinc. They can be employed in concentrations of $10^{-4}$ to $10^{-1}$ mol/liter and preferably of $10^{-3}$ to $10^{-2}$ mol/liter of impregnation solution.

Furthermore, in the production of the diagnostic agent according to the present invention, oxidation agents can additionally be used, for example potassium hexacyanoferrate III, potassium bromate, potassium chromate, phenazine-methosulphate or tetrazolium salts. These can be used in concentrations of $10^{-6}$ to 1 mol/liter and preferably of $10^{-3}$ to $10^{-1}$ mol/liter of impregnation solution, coating mass or fluid to be investigated.

For the production of the diagnostic agent according to the present invention, for example an absorbent carrier, preferably filter paper, cellulose or synthetic resin fiber fleece, is impregnated with solutions of the necessary reagents conventionally employed for the production of test strips (substrate, buffer, activators, optionally wetting agents, complex formers, oxidation agents, etc.) in readily volatile solvents, for example, water, methanol, ethanol or acetone. This impregnation is preferably carried out in two steps:

Impregnation is first carried out with an aqueous solution which contains the buffer and possibly water-soluble activators. Thereafter, impregnation is carried out with a solution which contains the esterase or protease substrate and possibly water-insoluble activators, as well as other water-insoluble additives. In special cases, the impregnation sequence can be reversed.

The finished test papers can be used as such or can, in known manner, be struck on to handles or preferably sealed between synthetic resins and fine-mesh fabrics in the manner described in Federal Republic of Germany Patent Specification No. 21 18 455.

For the production of film-coated test strips, all the reagents are introduced into a solution or dispersion of a film-forming substance, for example a polyvinyl ester or polyamide, and homogeneously mixed. The mixture is coated in a thin layer on to a synthetic resin carrier and dried. The film-coated test strips according to the present invention are, after drying, cut up and can be used as such or can be stuck, in known manner, on to handles or, for example, sealed between synthetic resins and fine-mesh fabrics in the manner described in Federal Republic of Germany Patent Specification No. 21 18 455.

The diagnostic agent according to the present invention for the detection of esterolytic and/or proteolytic enzymes in the form of powder mixtures or of reagent tablets can be produced by mixing the above-described components of the test with conventional galenical additives and granulated. Additives of this type include, for example, carbohydrates, such as mono-, oligo- and polysaccharides, and sugar alcohols, such as mannitol, sorbitol or xylitol, and other soluble, inert compounds, such as polyethylene glycol and polyvinylpyrrolidone. In general, the powder mixtures or reagent tablets have an end weight of about 50 to 200 mg. and preferably of 50 to 80 mg.

For the production of lyophilizates with a total weight of about 5 to 20 mg. and preferably of about 10 mg., a solution is freeze-dried which, in addition to the reagents needed for the test, contains conventional structure formers, for example polyvinylpyrrolidone, and possibly further filling materials, for example, mannitol, sorbitol or xylitol.

The diagnostic agent according to the present invention in the form of a solution preferably contains all the reagents needed for the test. As solvents, there can be used water or mixtures of water with a water-soluble organic solvent, for example, methanol, ethanol, acetone or dimethylformamide. For reasons of storage stability, it can be advantageous to divide the reagents needed for the test into two or more solutions which are only mixed at the time of carrying out the actual investigation.

The diagnostic agent produced in this manner enables leukocytes to be detected quickly and simply in body fluids to be investigated via a color formation or color change. In comparison with the diagnostic agents according to Federal Republic of Germany Patent Applications Nos. P 28 26 965.0, P 28 36 644.1 and P 28 54 987.3, when using the activators according to the present invention, considerably shortened reaction times are observed.

The following Examples are given for the purpose of illustrating the present invention:

EXAMPLE 1

Filter paper (for example Schleicher & Schüll 23 SL) is successively impregnated with the following solutions and then dried at 60° C. or at ambient temperature.

Solution 1 tris-(hydroxymethyl)-aminomethane hydrochloride buffer, 0.2 mol/liter, pH 9.0, in water Solution 2 substrate solution $10^{-3}$ mol/liter in acetone

The activators according to the present invention are, depending upon their solubility, added to Solution 1 or Solution 2 so that, in the case of activators of general formulae (I), (II) and (IV), there result end concentrations of $10^{-2}$ mol/liter of impregnation solution and in the case of activators of general formula (III), end concentrations of 2% (w/v) of the impregnation solution.

In the following Table 1, there are summarised the experimental results obtained with the following esterase or protease substrates;

A: diacetyl-3',3"-dibromo-5',5"-dichlorophenolsulphonphthalein,
B: diacetyl-4,5,6,7,3',5',3",5"-octabromophenolsulphonphthalein,
C: di-(N-benzylcarbonyl-L-alanyl)-3',5',3",5"-tetrabromophenolsulphonphthalein,
D: di-(N-benzyloxycarbonyl-L-phenylalanyl)-3',5',3",5"-tetrabromophenolsulphonphthalein.

In Table 1, the reaction times are given which extend from the dipping of the test strips into a standard solution containing 5000 leukocytes/μl. of isotonic sodium chloride solution up to the first distinct color reaction. As reference values, there are used the reaction times of the formulations in question but without the addition of activator. The color change in the case of the four compounds here investigated is from colorless to deep blue.

TABLE 1

| activators | reaction times for substrate | | | |
|---|---|---|---|---|
| | A sec. | B sec. | C sec. | D sec. |
| comparative formulation without activator | 210 | 90 | 600 | 550 |
| 1. pyridine | 110 | 70 | 410 | 450 |
| 2. 3-ethylpyridine | 95 | 65 | 440 | 470 |
| 3. 4-methoxypyridine | 110 | 65 | 470 | 450 |
| 4. quinoline | 75 | 50 | 320 | 340 |
| 5. 2-methylquinoline | 45 | 55 | 300 | 350 |
| 6. 4-bromoquinoline | 60 | 60 | 370 | 330 |
| 7. 3-methoxyquinoline | 50 | 50 | 310 | 380 |
| 8. isoquinoline | 85 | 55 | 350 | 380 |
| 9. benzo-[b]-quinoline (= acridine) | 90 | 65 | 280 | 330 |
| 10. benzo-[c]-quinoline (= phenanthridine) | 75 | 60 | 260 | 360 |
| 11. 2-methylphenanthridine | 100 | 65 | 250 | 370 |
| 12. 2-ethylphenanthridine | 80 | 70 | 300 | 360 |
| 13. 2-propylphenanthridine | 80 | 60 | 280 | 330 |
| 14. 2-methoxyphenanthridine | 85 | 60 | 260 | 350 |
| 15. benzo-[f]-quinoline | 90 | 40 | 310 | 310 |
| 16. benzo-[h]-quinoline | 90 | 55 | 290 | 340 |
| 17. 1,7-phenanthroline | 75 | 65 | 340 | 410 |
| 18. 4,7-phenanthroline | 80 | 70 | 270 | 380 |
| 19. 4-azafluorene | 120 | 50 | 240 | 290 |
| 20. quinine | 110 | 70 | 350 | 330 |
| 21. quinidine | 70 | 65 | 375 | 280 |
| 22. cinchonine | 60 | 50 | 340 | 300 |
| 23. cinchonidine | 65 | 55 | 390 | 320 |
| 24. cuprein | 70 | 60 | 400 | 305 |
| 25. 2-[phenyl]-vinyl-pyridine-(2') | 115 | 70 | 370 | 270 |
| 26. 2-[pyridyl-(3")]-vinyl-pyridine-(2') | 145 | 65 | 430 | 250 |
| 27. 2-[pyridyl-(4")]-vinyl-pyridine-(4') | 140 | 55 | 350 | 280 |
| 28. 2-[furyl-(2")]-vinyl-pyridine-(2') | 150 | 70 | 410 | 250 |
| 29. imidazole | 90 | 55 | 380 | 210 |
| 30. histamine | 110 | 60 | 440 | 290 |
| 31. (imidazolyl-4)-acetic acid | 150 | 75 | 450 | 350 |
| 32. β-(imidazolyl-4)-propionic acid | 170 | 70 | 490 | 380 |
| 33. L-histidine | 130 | 80 | 465 | 320 |
| 34. octan-1-ol | 150 | 75 | 500 | 460 |
| 35. decan-1-ol | 130 | 70 | 480 | 420 |
| 36. tetradecan-1-ol | 105 | 60 | 420 | 400 |
| 37. cyclooctanol | 125 | 80 | 530 | 480 |
| 38. cyclododecanol | 90 | 55 | 490 | 470 |
| 39. citronellol | 100 | 40 | 430 | 440 |
| 40. farnesol | 130 | 50 | 440 | 410 |
| 41. phytol | 135 | 55 | 430 | 450 |
| 42. tripotassiumhexacyanoferrate II | 160 | 70 | 550 | 480 |
| 43. dipotassiumtetracyanonickelate II | 160 | 80 | 530 | 450 |
| 44. disodium pentacyanonitrosyl-ferrate II | 150 | 65 | 470 | 460 |

Similar experimental results are obtained when, instead of substrates A, B, C and D, there are used other sulphonphthalein esters of Federal Republic of Germany Patent Application No. P 28 26 965.0 and/or when, instead of a standard solution of 5000 leukocytes/μl. of isotonic sodium chloride solution, leukocyte-containing urines are used.

EXAMPLE 2

Filter paper (for example Schleicher & Schüll 23 SL) is successively impregnated with the following solutions and then dried at 60° C. or at ambient temperature.

Solution 1 tris-(hydroxymethyl)-aminomethane hydrochloride buffer, 0.2 mol/liter, pH 7.0, in water (for substrates E, F and G), or
tris-(hydroxymethyl)-aminomethane hydrochloride buffer, 0.2 mol/liter, pH 8.0, in water (for substrate H).

Solution 2 substrate solutions $10^{-3}$ mol/liter in acetone.

Activator additions and the carrying out of the experiments take place as in Example 1.

The following Table 2 summarizes the experimental results obtained with the following protease substrates:

E: thiazole-2-azo-4'-[1'-(N-benzyloxycarbonyl-L-alanyloxy)-5'-methoxynaphthalene]
(color change of the test paper from pink to red)
F: 6-methoxybenzothiazole-2-azo-2'-[1'-(N-benzyloxycarbonyl-L-alanyloxy)-naphthalene]
(color change of the test paper from pink to red)
G: 2,4-dinitrobenzeneazo-4'-[1'-(N-benzyloxycarbonyl-L-alanyloxy)-benzene]
(color change of the test paper from yellow to red-violet)
H: 2,5-dimethoxybenzeneazo-4'-[1'-(N-benzyloxycarbonyl-L-alanyloxy)-naphthalene]
(color change of the test paper from bright orange to red)

The reaction times are given which extend from the dipping of the test paper into a standard solution of 5000 leukocytes/μl. of isotonic sodium chloride solution up to the first distinct color reaction. As reference values, there serve the reaction times of the corresponding formulations without the addition of activators.

TABLE 2

| activators | reaction times for substrate | | | |
|---|---|---|---|---|
| | E sec. | F sec. | G sec. | H sec. |
| comparative formulation without activator | 60 | 180 | 160 | 70 |
| 1. pyridine | 50 | 150 | 130 | 55 |
| 2. 2-methylpyridine | 45 | 140 | 135 | 50 |
| 3. 2-bromopyridine | 50 | 150 | 125 | 45 |
| 4. 3,5-dichloropyridine | 45 | 160 | 130 | 50 |

TABLE 2-continued

| activators | reaction times for substrate | | | |
|---|---|---|---|---|
| | E sec. | F sec. | G sec. | H sec. |
| 5. quinoline | 50 | 110 | 95 | 45 |
| 6. 8-methylquinoline | 45 | 130 | 110 | 40 |
| 7. 2-chloroquinoline | 40 | 130 | 110 | 35 |
| 8. 6-ethoxyquinoline | 35 | 150 | 120 | 40 |
| 9. 2-methyl-4-methoxy-quinoline | 40 | 120 | 105 | 40 |
| 10. isoquinoline | 40 | 130 | 110 | 40 |
| 11. 1-methylisoquinoline | 45 | 100 | 120 | 35 |
| 12. 4-bromoisoquinoline | 45 | 140 | 115 | 40 |
| 13. 7-methoxyisoquinoline | 50 | 130 | 130 | 45 |
| 14. benzo-[b]-quinoline (acridine) | 30 | 150 | 60 | 45 |
| 15. benzo-[c]-quinoline (phenanthridine) | 35 | 120 | 80 | 40 |
| 16. 2-methylphenanthridine | 40 | 140 | 90 | 40 |
| 17. benzo-[f]-quinoline | 50 | 130 | 70 | 30 |
| 18. 2-isopropyl-benzo-[f]-quinoline | 45 | 130 | 95 | 35 |
| 19. 3-methyl-benzo-[f]-quinoline | 40 | 125 | 80 | 40 |
| 20. 2,4-dimethylbenzo-[f]-quinoline | 40 | 110 | 90 | 40 |
| 21. benzo-[g]-quinoline | 40 | 90 | 70 | 35 |
| 22. 4-methylbenzo-[g]-quinoline | 40 | 100 | 80 | 40 |
| 23. benzo-[h]-quinoline | 35 | 70 | 50 | 30 |
| 24. 1,7-phenanthroline | 45 | 120 | 120 | 40 |
| 25. 4,7-phenanthroline | 40 | 105 | 105 | 45 |
| 26. 1,10-phenanthroline | 45 | 130 | 110 | 45 |
| 27. quinine | 40 | 120 | 60 | 35 |
| 28. cinchonine | 45 | 100 | 90 | 30 |
| 29. cuprein | 40 | 140 | 105 | 30 |
| 30. 2-[phenyl]-vinyl-pyridine-(2') | 35 | 125 | 120 | 50 |
| 31. bis-[2-(phenyl)-vinyl]-pyridine-(2',4') | 30 | 150 | 140 | 60 |
| 32. 2-[furyl-(2″)]-vinyl-pyridine-(2') | 30 | 120 | 90 | 55 |
| 33. imidazole | 45 | 140 | 120 | 40 |
| 34. 1-ethylimidazole | 40 | 130 | 130 | 45 |
| 35. 1-phenylimidazole | 35 | 120 | 120 | 40 |
| 36. 1-(4'-hydroxyphenyl)-imidazole | 45 | 140 | 135 | 50 |
| 37. histamine | 50 | 130 | 140 | 55 |
| 38. β-(imidazolyl-4)-propionic acid | 50 | 150 | 140 | 50 |
| 39. β-(imidazolyl-4)-acrylic acid | 50 | 160 | 135 | 55 |
| 40. L-histidine | 45 | 150 | 125 | 50 |
| 41. N-α-acetyl-L-histidine | 45 | 140 | 130 | 40 |
| 42. heptan-1-ol | 30 | 130 | 100 | 40 |
| 43. octan-1-ol | 30 | 120 | 95 | 35 |
| 44. decan-1-ol | 20 | 90 | 80 | 30 |
| 45. dodecan-1-ol | 20 | 80 | 70 | 30 |
| 46. hexadecan-1-ol | 25 | 105 | 80 | 40 |
| 47. eicosan-1-ol | 30 | 120 | 110 | 45 |
| 48. cyclohexanol | 35 | 110 | 105 | 40 |
| 49. cyclodecanol | 25 | 95 | 85 | 30 |
| 50. cyclododecanol | 25 | 120 | 90 | 25 |
| 51. cycloheptadecanol | 30 | 130 | 120 | 30 |
| 52. cycloheptadec-9-en-1-ol | 30 | 110 | 100 | 35 |
| 53. citronellol | 25 | 100 | 70 | 25 |
| 54. linalool | 20 | 105 | 60 | 30 |
| 55. farnesol | 30 | 110 | 75 | 25 |
| 56. cis-octadec-9-en-1-ol | 25 | 90 | 85 | 40 |
| 57. phytol | 30 | 80 | 65 | 30 |
| 58. pentane-1,5-diol | 35 | 130 | 120 | 45 |
| 59. heptane-1,7-diol | 40 | 150 | 125 | 40 |
| 60. decane-1,10-diol | 30 | 135 | 140 | 50 |
| 61. dodecane-1,12-diol | 40 | 160 | 130 | 50 |
| 62. tripotassium hexacyanoferrate III | 45 | 160 | 135 | 55 |
| 63. tetrapotassium hexacyanoferrate II | 40 | 160 | 140 | 50 |
| 64. disodium pentacyanonitrosyl-ferrate II | 40 | 140 | 130 | 40 |
| 65. tripotassium pentacyanonitrosyl-chromate I | 50 | 145 | 130 | 50 |
| 66. tripotassium pentacyanonitrosyl-cobaltate I | 50 | 160 | 145 | 45 |

Similar experimental results are achieved when, instead of substrates E, F, G and H, there are used other azo dyestuff esters of Federal Republic of Germany Patent Application No. P 28 36 644.1 and/or when instead of the standard solution of 5000 leukocytes/μl. isotonic sodium chloride solution, leukocyte-containing urines are used.

EXAMPLE 3

Filter paper (for example Schleicher & Schüll 23 SL) is successively impregnated with the following solutions and then dried at 60° C. or ambient temperature.

Solution 1 sodium tetraborate hydrochloric acid buffer, 0.2 mol/liter, pH 8.0, in water

Solution 2 substrate solution $10^{-3}$ mol/liter in acetone

Activator additions and the carrying out of the experiments take place as in Example 1.

In the following Table 3, there are summarized the experimental results obtained with the following protease substrates:

I: 3-[N-(diphenylcarbamoyl)-L-alanyloxy]-indole
J: 3-[N-(5',5'-dimethyl-3'-oxo-cyclohex-1'-enyl)-L-alanyloxy]-indole
K: 3-[N-(benzyloxycarbonyl)-L-alanyloxy]-indole The reaction times are given which extend from the dipping of the test strips into a standard solution of 5000 leukocytes/μl. of isotonic sodium chloride solution up to the first distinct color reaction. The reaction times of the formulations in question without the additions of activator serve as reference values.

The test papers produced with the three substrates give, after dipping into leukocyte-containing solutions, colour changes from colorless to deep blue.

TABLE 3

| activators | reaction times for substrate | | |
|---|---|---|---|
| | I sec. | J sec. | K sec. |
| comparative formulation without activator | 300 | 180 | 60 |
| 1. pyridine | 220 | 140 | 45 |
| 2. 2-bromopyridine | 205 | 130 | 40 |
| 3. 2,6-dimethyl-4-ethoxy-pyridine | 160 | 110 | 40 |
| 4. quinoline | 185 | 90 | 35 |
| 5. 2-methylquinoline | 190 | 105 | 40 |
| 6. 7-isopropylquinoline | 165 | 80 | 35 |
| 7. 3-methoxyquinoline | 150 | 75 | 30 |
| 8. 2-methyl-6-bromoquinoline | 170 | 80 | 40 |
| 9. 5,7-dibromo-8-methoxy-quinoline | 195 | 90 | 40 |
| 10. isoquinoline | 150 | 80 | 40 |
| 11. 3-propylisoquinoline | 170 | 75 | 35 |
| 12. 7-methylisoquinoline | 145 | 105 | 30 |
| 13. 1-chloroisoquinoline | 180 | 90 | 35 |
| 14. 1-methoxy-3-chloro-isoquinoline | 155 | 95 | 40 |
| 15. 1-chloro-4-methyl-5-methoxy- | 190 | 80 | 35 |

TABLE 3-continued

| activators | reaction times for substrate I sec. | J sec. | K sec. |
|---|---|---|---|
| isoquinoline | | | |
| 16. benzo-[b]-quinoline (acridine) | 170 | 90 | 40 |
| 17. benzo-[c]-quinoline (phenanthridine) | 130 | 110 | 35 |
| 18. 2-ethylphenanthridine | 160 | 100 | 30 |
| 19. 2-methoxyphenanthridine | 145 | 120 | 35 |
| 20. benzo-[f]-quinoline | 130 | 105 | 35 |
| 21. benzo-[g]-quinoline | 140 | 130 | 45 |
| 22. 2,4-dimethyl-benzo-[g]-quinoline | 135 | 110 | 40 |
| 23. benzo-[h]-quinoline | 110 | 70 | 40 |
| 24. 1,7-phenanthroline | 165 | 130 | 45 |
| 25. 2-methyl-1,7-phenanthroline | 130 | 110 | 45 |
| 26. 2,8-dimethyl-1,7-phenanthroline | 145 | 105 | 40 |
| 27. 4,7-phenanthroline | 120 | 120 | 35 |
| 28. 3-methyl-4,7-phenanthroline | 145 | 95 | 40 |
| 29. 3,8-dimethyl-4,7-phenanthroline | 160 | 80 | 35 |
| 30. 1,10-phenanthroline | 170 | 90 | 35 |
| 31. 2,9-dimethyl-1,10-phenanthroline | 145 | 120 | 45 |
| 32. 4-azafluorene | 90 | 60 | 35 |
| 33. quinine | 150 | 90 | 30 |
| 34. cinchonidine | 125 | 85 | 30 |
| 35. cuprein | 160 | 95 | 35 |
| 36. 2-[4″-methoxyphenyl]-vinyl-pyridine-(2′) | 95 | 90 | 45 |
| 37. 2-[4″-(N,N-dimethylamino)-phenyl]-vinyl-pyridine-(2′) | 110 | 110 | 45 |
| 38. bis-[2-(phenyl)-vinyl]-pyridine-(2′,4′) | 120 | 95 | 40 |
| 39. 2-[naphthyl-(1″)]-vinyl-pyridine-(2′) | 105 | 90 | 40 |
| 40. 2-[pyridyl-(2″)]-vinyl-pyridine-(2′) | 80 | 80 | 30 |
| 41. 2-[pyridyl-(4″)]-vinyl-pyridine-(2′) | 60 | 50 | 25 |
| 42. 2-[pyridyl-(3″)]-vinyl-pyridine-(3′) | 75 | 70 | 30 |
| 43. 2-[pyridyl-(3″)]-vinyl-pyridine-(4′) | 95 | 90 | 25 |
| 44. 2-[thienyl-(2″)]-vinyl-pyridine-(4′) | 80 | 75 | 35 |
| 45. imidazole | 175 | 120 | 35 |
| 46. 1-phenylimidazole | 180 | 140 | 40 |
| 47. histamine | 230 | 150 | 45 |
| 48. N-α-acetyl-histamine | 205 | 130 | 40 |
| 49. (imidazolyl-4)-acetic acid | 220 | 150 | 50 |
| 50. L-histidine | 195 | 120 | 45 |
| 51. N-α-acetyl-L-histidine | 165 | 110 | 40 |
| 52. hexan-1-ol | 95 | 95 | 30 |
| 53. octan-1-ol | 90 | 100 | 30 |
| 54. nonan-1-ol | 90 | 80 | 30 |
| 55. decan-1-ol | 80 | 60 | 25 |
| 56. dodecan-1-ol | 75 | 90 | 25 |
| 57. pentadecan-1-ol | 100 | 80 | 30 |
| 58. heptadecan-1-ol | 80 | 105 | 35 |
| 59. octadecan-1-ol | 90 | 95 | 40 |
| 60. nonadecan-1-ol | 85 | 120 | 40 |
| 61. docosan-1-ol | 85 | 110 | 40 |
| 62. cyclohex-1-en-1-ol | 95 | 130 | 35 |
| 63. cyclononanol | 80 | 120 | 35 |
| 64. cyclodecanol | 80 | 115 | 40 |
| 65. cycloheptadecanol | 90 | 130 | 40 |
| 66. geraniol | 75 | 85 | 30 |
| 67. nerol | 90 | 70 | 35 |
| 68. linalool | 80 | 80 | 30 |
| 69. nerolidol | 105 | 90 | 25 |
| 70. cis-octadec-9-en-1-ol | 110 | 115 | 25 |
| 71. hexane-1,6-diol | 130 | 130 | 45 |
| 72. octane-1,8-diol | 115 | 125 | 40 |
| 73. nonane-1,9-diol | 140 | 130 | 45 |
| 74. decane-1,10-diol | 130 | 115 | 50 |
| 75. tetrapotassium hexacyanoferrate II | 230 | 160 | 50 |
| 76. trisodium octacyanomolybdate V | 205 | 150 | 50 |
| 77. tripotassium pentacyanonitrosyl-ferrate II | 180 | 150 | 45 |
| 78. tripotassium pentacyanonitrosyl-manganate I | 210 | 145 | 40 |
| 79. pentapotassium pentacyanonitrosyl-vanadate I | 220 | 155 | 45 |

Similar results are obtained with other indoxyl esters of Federal Republic of Germany Patent Application No. P 28 54 987.3 and/or with leukocyte-containing urines instead of the standard solution of 5000 leukocytes/μl. isotonic sodium chloride solution.

EXAMPLE 4

Filter paper (for example Schleicher & Schüll 23 SL) is successively impregnated with the following solutions and then dried at 60° C. or at ambient temperature:

Solution 1 tris-(hydroxymethyl)-aminomethane hydrochloride buffer, 0.2 mol/liter, pH 9.0, in water

Solution 2 diacetyl-3′,5′,3″,5″-tetrabromophenylsulphonphthalein, $10^{-3}$ mol/liter in acetone.

The activators according to the present invention are added individually or as mixtures, depending upon the solubility, to Solution 1 and/or Solution 2 so that, in the case of the individual activators of general formulae (I), (II) and (IV), there result end concentrations of $10^{-2}$ mol/liter of impregnation solution and in the case of activators of general formula (III) end concentrations of 2% (w/v) of the impregnation solution.

In the following Table 4, there are summarized the reaction times which extend from the dipping in of the test strips into a standard solution of 5000 leukocytes/μl. isotonic sodium chloride solution up to the first distinct color reaction. The reaction time of the formulation without the addition of activator serves as reference value.

Upon dipping into leukocyte-containing solutions, the test papers change from colourless to deep blue.

TABLE 4

| activators | reaction times |
|---|---|
| comparative formulation without activators | 160 sec. |
| 1. 2-methylquinoline | 110 sec. |
| 2. tetradecan-1-ol | 90 sec. |
| activators 1 and 2 | 60 sec. |
| 3. 1,7-phenanthroline | 80 sec. |
| 4. tetrapotassium hexacyanoferrate II | 140 sec. |
| activators 3 and 4 | |
| 5. cinchonine | 90 sec. |
| 6. 2-[phenyl]-vinyl-pyridine-(2′) | 105 sec. |
| activators 5 and 6 | 65 sec. |

Similar experimental results are obtained with leukocyte-containing urines instead of the standard solution of 5000 leukocytes/μl. isotonic sodium chloride solution.

EXAMPLE 5

Test papers are produced in the manner described in Example 4, using the following solutions:

Solution 1 tris-(hydroxymethyl)-aminomethane hydrochloride buffer, 0.2 mol/liter, pH 8.0, in water

Solution 2

2-methoxy-4-nitrobenzeneazo-4'-[1'-(N-benzyloxycarbonyl-L-alanyloxy)-naphthalene], $10^{-3}$ mol/liter in acetone.

Upon dipping into leukocyte-containing solutions, the test papers change color from bright orange to red.

In the following Table 5, there are given the experimental results. The reaction times are given which extend from the dipping of the test strips into a standard solution of 5000 leukocytes/μl. of isotonic sodium chloride solution up to the first distinct color reaction. The reaction time of the formulation without the addition of activator serves as reference value.

TABLE 5

| activators | reaction times |
|---|---|
| comparative formulation without activator | 80 sec. |
| 1. benzo-[b]-quinoline (acridine) | 60 sec. |
| 2. cis-octadec-9-en-1-ol | 40 sec. |
| activators 1 and 2 | 30 sec. |
| 3. benzo-[h]-quinoline | 50 sec. |
| 4. quinine | 55 sec. |
| activators 3 and 4 | 35 sec. |
| 5. 1,7-phenanthroline | 45 sec. |
| 6. farnesol | 30 sec. |
| activators 5 and 6 | 25 sec. |

Similar experimental results are achieved with the use of leukocyte-containing urines instead of the standard solution of 5000 leukocytes/μl. of isotonic sodium chloride solution.

EXAMPLE 6

Test papers are produced in the manner described in Example 4, using the following solutions:

Solution 1 sodium tetraborate hydrochloric acid buffer, 0.2 mol/liter, pH 8.0, in water

Solution 2

3-[N-(2'-nitrobenzenesulphenyl)-L-alanyloxy]-indole, $10^{-3}$ mol/liter, in acetone.

Upon dipping into leukocyte-containing solutions, the test papers change color from yellow to green.

The experimental results obtained are summarized in the following Table 6. The reaction times are given which extend from the dipping of the test strips into a standard solution of 5000 leukocytes/μl. isotonic sodium chloride solution up to the first distinct color reaction. The reaction time of the formulation without the addition of activator serves as reference value.

TABLE 6

| activators | reaction times |
|---|---|
| comparative formulation without activators | 100 sec. |
| 1. quinoline | 80 sec. |
| 2. cyclododecanol | 70 sec. |
| activators 1 and 2 | 55 sec. |
| 3. 2-[furyl-(2")]-vinyl-pyridine-(2') | 75 sec. |
| 4. phytol | 50 sec. |
| activators 3 and 4 | 40 sec. |
| 5. 4,7-phenanthroline | 85 sec. |
| 6. tetrapotassium hexacyanoferrate II | 90 sec. |
| activators 5 and 6 | 70 sec. |

Similar experimental results are obtained with leukocyte-containing urines instead of the standard solution of 5000 leukocytes/μl. of isotonic sodium chloride solution.

EXAMPLE 7

Test papers are produced in the manner described in Example 4 with the following solutions:

Solution 1 sodium tetraborate hydrochloric acid buffer, 0.2 mol/liter, pH 8.0, in water

Solution 2

3-[N-(benzoyl)-D,L-alanyloxy]-indole, $10^{-3}$ mol/liter, in acetone.

Upon dipping into leukocyte-containing solutions, the test papers change color from colorless to blue.

The experimental results obtained are summarized in the following Table 7. The reaction times are given which extend from the dipping of the test strips into a standard solution of 5000 leukocytes/μl. of isotonic sodium chloride solution up to the first distinct color reaction. The reaction time of the formulation without the addition of activator serves as reference value.

TABLE 7

| activators | reaction times |
|---|---|
| comparative formulation without activators | 90 sec. |
| 1. 2-[phenyl]-vinyl-pyridine-(2') | 70 sec. |
| 2. hexadecan-1-ol | 55 sec. |
| activators 1 and 2 | 40 sec. |
| 3. 2-[pyridyl-4(")]-vinyl-pyridine-(4') | 40 sec. |
| 4. linalool | 50 sec. |
| activators 3 and 4 | 30 sec. |
| 5. cinchonine | 75 sec. |
| 6. disodium pentacyanonitrosylferrate II | 60 sec. |
| activators 5 and 6 | 40 sec. |

Similar experimental results are obtained with leukocyte-containing urines instead of the standard solution of 5000 leukocytes/μl. of isotonic sodium chloride solution.

EXAMPLE 8

Test papers are produced in the manner described in Example 4 with the following solutions:

Solution 1 sodium tetraborate hydrochloric acid buffer, 0.2 mol/liter, pH 8.0, in water

Solution 2

3-[N-(toluene-4'-sulphonyl)-L-alanyloxy]-indole, $10^{-3}$ mol/liter, in acetone.

Upon dipping into leukocyte-containing solutions, the test papers change color from colorless to blue.

The experimental results obtained are summarized in the following Table 8. The reaction times are given which extend from the dipping of the test strips into a standard solution of 5000 leukocytes/$\mu$l. of isotonic sodium chloride solution up to the first distinct color reaction. The reaction time of the formulation without the addition of activator serves as a reference value.

TABLE 8

| activators | reaction times |
|---|---|
| comparative formulation without activators | 24 sec. |
| 1. quinine | 22 sec. |
| 2. disodium pentacyanonitrosyl-ferrate II | 15 sec. |
| 3. decan-1-ol | 18 sec. |
| activators 1, 2 and 3 | 6 sec. |

Similar results are obtained with leukocyte-containing urines instead of the standard solution of 5000 leukocytes/$\mu$l. of isotonic sodium chloride solution.

EXAMPLE 9

Filter paper (for example Schleicher & Schüll 23 SL) is successively impregnated with the following solutions and then dried at 60° C. or at ambient temperature:

Solution 1 laurylpyridinium chloride, 0.2%, in tris-(hydroxymethyl)aminomethane hydrochloride buffer, 0.2 mol/liter, pH 7.0, in water Solution 2 thiazole-2-azo-4'-[1'-(N-benzyloxycarbonyl-L-alanyloxy)naphthalene], $10^{-3}$ mol/liter, in acetone.

The activator addition and the carrying out of the experiment take place as in Example 1.

Upon dipping into leukocyte-containing solutions, the test papers change color from pink to violet.

The experimental results obtained are summarized in the following Table 9. The reaction times are given which extend from the dipping of the test strips into a standard solution of 5000 leukocytes/$\mu$l. of isotonic sodium chloride solution up to the first distinct color reaction. The reaction time of the formulation without the addition of activator serves as reference value.

TABLE 9

| activators | reaction times |
|---|---|
| comparative formulation without activator | 70 sec. |
| 1. pyridine | 45 sec. |
| 2. quinoline | 40 sec. |
| 3. benzo-[b]-quinoline (acridine) | 35 sec. |
| 4. 1,10-phenanthroline | 40 sec. |
| 5. 4-azafluorene | 30 sec. |
| 6. quinine | 35 sec. |
| 7. 2-[pyridyl-(4")]-vinyl-pyridine-(4') | 30 sec. |
| 8. imidazole | 50 sec. |
| 9. dodecan-1-ol | 30 sec. |
| 10. phytol | 25 sec. |
| 11. disodium pentacyanonitrosyl-ferrate II | 60 sec. |

Similar experimental results are obtained with the other substrates and activators mentioned in Examples 1 to 7 and/or with other conventional wetting agents.

EXAMPLE 10

Filter paper (for example Schleicher & Schüll 23 SL) is successively impregnated with the following solutions and then dried at 60° C. or at ambient temperature.

Solution 1 tris-(hydroxymethyl)-aminomethane hydrochloride buffer, 0.2 mol/liter, pH 7.0, in water Solution 2 thiazole-2-azo-1'-[2'-(N-benzyloxycarbonyl-L-alanyloxy)-naphthalene], $10^{-3}$ mol/liter, and zinc acetate dihydrate, $10^{-3}$ mol/liter, in acetone.

The activator addition and the carrying out of the experiment take place as in Example 1.

Upon dipping into leukocyte-containing solutions, the test papers change color from pink to blue-violet.

The experimental results obtained are summarized in the following Table 10. The reaction times are given which extend from the dipping of the test strips into a standard solution of 5000 leukocytes/$\mu$l. of isotonic sodium chloride solution up to the first distinct color reaction. The reaction time of the formulation without the addition of activator serves as reference value.

TABLE 10

| activators | reaction times |
|---|---|
| comparative formulation without activator | 65 sec. |
| 1. pyridine | 50 sec. |
| 2. quinoline | 45 sec. |
| 3. benzo-[b]-quinoline (acridine) | 40 sec. |
| 4. 1,10-phenanthroline | 30 sec. |
| 5. 4-azafluorene | 35 sec. |
| 6. quinine | 30 sec. |
| 7. 2-[pyridyl-(4")]-vinyl-pyridine-(4') | 35 sec. |
| 8. imidazole | 45 sec. |
| 9. dodecan-1-ol | 25 sec. |
| 10. phytol | 30 sec. |
| 11. disodium pentacyano-nitrosyl-ferrate II | 50 sec. |

Similar experimental results are obtained with other azo dyestuff esters of Federal Republic of Germany Patent Application No. P 28 36 644.1, with other activators mentioned in Examples 1 to 7 and/or with other conventional complex formers.

EXAMPLE 11

Filter paper (for example Schleicher & Schüll 23 SL) is successively impregnated with the following solutions and then dried at 60° C. or at ambient temperature.

Solution 1 potassium bromate, $10^{-2}$ mol/liter, in sodium tetraborate hydrochloric acid buffer, 0.2 mol/liter, pH 8.0, in water.

Solution 2

3-[N-formyl-L-alanyloxy]-indole, $10^{-3}$ mol/liter, in acetone.

The addition of activator and the carrying out of the experiment take place as in Example 1.

Upon dipping into leukocyte-containing solutions, the test papers change color from colorless to blue.

The experimental results obtained are summarized in the following Table 11. The reaction times are given which extend from the dipping of the test papers into a standard solution of 5000 leukocytes/μl. of isotonic sodium chloride solution up to the first distinct color reaction. The reaction time of the formulation without the addition of activator serves as reference value.

TABLE 11

| activators | reaction times |
|---|---|
| comparative formulation without activators | 120 sec. |
| 1. pyridine | 85 sec. |
| 2. quinoline | 70 sec. |
| 3. benzo-[b]-quinoline (acridine) | 100 sec. |
| 4. 1,10-phenanthroline | 65 sec. |
| 5. 4-azafluorene | 50 sec. |
| 6. quinine | 75 sec. |
| 7. 2-[pyridyl-(4")]-vinyl-pyridine-(4') | 70 sec. |
| 8. imidazole | 85 sec. |
| 9. dodecan-1-ol | 35 sec. |
| 10. phytol | 40 sec. |
| 11. disodium pentacyano-nitrosyl-ferrate II | 90 sec. |

Similar experimental results are also obtained with other indoxyl esters of Federal Republic of Germany Patent Application No. P 28 54 987.3, with the other activators described in Examples 1 to 7 and with other conventional oxidation agents.

It will be understood that the specification and examples are illustrative but not limitative of the present invention and that other embodiments within the spirit and scope of the invention will suggest themselves to those skilled in the art.

What is claimed is:

1. Diagnostic agent for the detection of esterolytic and proteolytic enzymes in body fluids, which agent comprises at least one substrate, and adjuvants suitable for said substrate, and at least one activator, and wherein said substrate is a sulphonphthalein ester of the formula

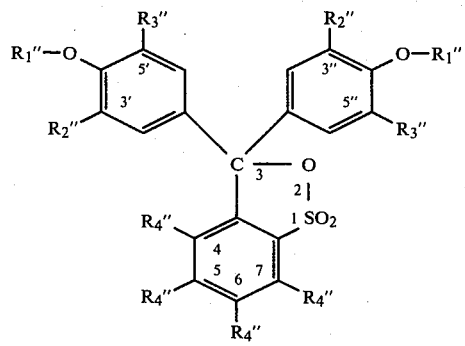

wherein $R_1''$ is a carboxylic acid residue optionally substituted by halogen or a lower alkoxy radical or is an amino acid or peptide residue provided with a nitrogen protective group conventional in peptide chemistry;

$R_2''$ is a halogen atom or a lower alkyl radical; and $R_3''$ and $R_4''$, which can be the same or different are hydrogen or halogen atoms; or an azo dyestuff ester of the formula

A'—N=N—B'(OR)$_n$ wherein

A' is a five- or six-membered, optionally benzo-annellated residue with one or two heteroatoms selected from nitrogen, sulfur and oxygen, which is optionally substituted one or more times by halogen, lower alkyl or lower alkoxy radicals or is a phenyl radical substituted one, two or three times by lower alkyl, lower alkoxy, nitro, sulphonato or acylamino radicals;

B' is a benzene, naphthalene or quinoline radical optionally substituted once or twice by sulphonato, lower alkoxy or lower alkoxypolyalkyleneoxy radicals;

R is a carboxylic acid residue or an amino acid or peptide residue provided with a nitrogen protective group conventional in peptide chemistry; and n is 1 or 2; or an indoxyl ester of the formula

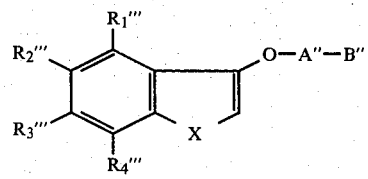

wherein $R_1'''$, $R_2'''$, $R_3'''$ and $R_4'''$, which can be the same or different, are hydrogen or halogen atoms, lower alkyl, lower alkoxy, aryl, aralkyl, aralkoxy, hydroxyl, carboxy, carboxy lower alkoxy, aralkoxycarbonyl, aralkoxycarbonyl lower alkoxy, nitro or lower acylamino radicals or in which two adjacent substituents represent a benzo-annellated residue optionally substituted by halogen;

X is a sulfur atom or an imino group optionally substituted by a lower alkyl, aryl, aralkyl or acyl radical;

A" is an amino acid or peptide residue; and

B" is a nitrogen protective group conventional in peptide chemistry or derived therefrom.

and said activator is selected from the following:

(a) pyridine derivatives of the general formula:

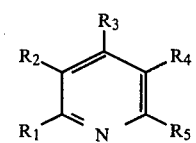

in which $R_1$, $R_2$, $R_3$, $R_4$ and $R_5$, which can be the same or different, are hydrogen or halogen atoms, lower alkyl or lower alkoxy radicals, vinyl radicals which are substituted by an aryl radical optionally substituted one or more times by lower alkoxy, amino, alkylamino or dialkylamino, or by a heterocyclic radical, whereby two adjacent substituents can represent an indeno- or benzo-annellated residue optionally substituted one or more times by halogen, hydroxyl, lower alkyl or lower alkoxy, which annellated residue can, in turn, carry a benzo- or pyrido-annellated residue optionally substituted by a lower alkyl radical and $R_3$ can also stand for a vinylquinuclidyl-carbinol radical;

(b) imidazole derivatives of the general formula:

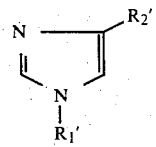

in which R₁' is a hydrogen atom, a lower alkyl radical or an aryl radical optionally substituted by a hydroxyl group or an acyl radical and R₂' is a hydrogen atom, an aminoalkyl, N-acylaminoalkyl or a lower aliphatic, optionally unsaturated carboxylic acid residue or a lower aliphatic α-amino acid residue optionally acylated on the nitrogen;
(c) alcohols of the general formula:

X—A—OH in which X is a hydrogen atom or a hydroxyl group and A is a hydrocarbon radical;
(d) metal complexes of the general formula:

$D_m[B(CN)_n(NO)_p]$ in which D is an alkali metal ion, B is a heavy metal ion, m is 2, 3, 4 or 5, n is 4, 5, 6, 7 or 8 and p is 0 or 1, the number m being given by the valency of the heavy metal ion and the number n.

2. Diagnostic agent as claimed in claim 1 wherein said conventional adjuvants are selected from buffers, complex formers, wetting agents, oxidation agents, film formers, galenical additional materials and structure formers.

3. Diagnostic agent as claimed in claim 1 wherein said activator is a pyridine derivative (a).

4. Diagnostic agent as claimed in claim 1 wherein said activator is an imidazole derivative (b).

5. Diagnostic agent as claimed in claim 1 wherein said activator is an alcohol (c).

6. Diagnostic agent as claimed in claim 1 wherein said activator is a metal complex (d).

7. Diagnostic agent as claimed in claim 1 wherein said activator is benzo-[h]-quinoline.

8. Diagnostic agent as claimed in claim 1 wherein said activator is 4-azafluorene.

9. Diagnostic agent as claimed in claim 1 wherein said activator is quinine.

10. Diagnostic agent as claimed in claim 1 wherein said activator is 2-[phenyl]-vinyl-pyridine-(2').

11. Diagnostic agent as claimed in claim 1 wherein said activator is imidazole.

12. Diagnostic agent as claimed in claim 1 wherein said activator is histamine.

13. Diagnostic agent as claimed in claim 1 wherein said activator is decan-1-ol.

14. Diagnostic agent as claimed in claim 1 wherein said activator is tetradecan-1-ol.

15. Diagnostic agent as claimed in claim 1 wherein said activator is tripotassium-hexacyanoferrate III.

16. Diagnostic agent as claimed in claim 1 wherein said activator is disodium-pentacyano-nitrosylferrate II.

17. Method of detecting leukocytes in body fluid which method comprises contacting a sample with a diagnostic agent as claimed in claim 1.

18. Method as claimed in claim 17 wherein said body fluid is urine.

19. Method as claimed in claim 17 wherein said activator is selected from
benzo-[h]-quinoline;
4-azafluorene;
quinine;
2-[phenyl]-vinyl-pyridine-(2');
imidazole;
histamine;
decan-1-ol;
tetradecan-1-ol;
tripotassium-hexacyanoferrate III; and
disodium-pentacyano-nitrosylferrate II.

20. Method as claimed in claim 17 wherein said activator is quinine.

21. Method as claimed in claim 17 wherein said activator is decan-1-ol.

22. Method as claimed in claim 17 wherein said activator is disodium-pentacyano-nitrosylferrate II.

23. Process for preparing a diagnostic agent as claimed in claim 1 which process comprises impregnating an absorbent carrier with at least one said substrate selected from said esterase and protease substrates, with conventional adjuvants, and additionally with at least one said activator.

24. Process as claimed in claim 23 wherein said absorbent carrier is impregnated in two stages.

* * * * *

UNITED STATES PATENT AND TRADEMARK OFFICE
CERTIFICATE OF CORRECTION

PATENT NO. : 4,299,917

DATED : November 10, 1981

INVENTOR(S) : Dieter Berger et al.

It is certified that error appears in the above-identified patent and that said Letters Patent is hereby corrected as shown below:

Column 2, line 34     Delete "sulphonate" and insert -- sulphonato --.

Column 4, line 42     Delete "hereto" and insert -- hetero --.

Column 14, line 59    After "activators 3 and 4" insert -- 70 sec. --.

Signed and Sealed this

Thirteenth Day of December 1983

[SEAL]

Attest:

Attesting Officer

GERALD J. MOSSINGHOFF

Commissioner of Patents and Trademarks